US012740921B1

(12) United States Patent
Qin et al.

(10) Patent No.: US 12,740,921 B1
(45) Date of Patent: Sep. 22, 2026

(54) GINGIVAL BARRIER PROTECTIVE RESIN

(71) Applicant: Jiangxi Dentalbright Technology Co., Ltd., Jiujiang (CN)

(72) Inventors: Junyuan Qin, Jiujiang (CN); Wei Min, Jiujiang (CN); Juan Huang, Jiujiang (CN)

(73) Assignee: Jiangxi Dentalbright Technology Co., Ltd., Jiujiang (CN)

( * ) Notice: Subject to any disclaimer, the term of this patent is extended or adjusted under 35 U.S.C. 154(b) by 0 days.

(21) Appl. No.: 19/450,901

(22) Filed: Jan. 16, 2026

(30) Foreign Application Priority Data

Dec. 29, 2025 (CN) ......................... 202512002517.5

(51) Int. Cl.
*A61K 6/60* (2020.01)
*A61K 6/20* (2020.01)
*A61K 6/62* (2020.01)
*A61K 6/76* (2020.01)
*A61K 6/77* (2020.01)
*A61K 6/78* (2020.01)

(52) U.S. Cl.
CPC .................. *A61K 6/20* (2020.01); *A61K 6/62* (2020.01); *A61K 6/76* (2020.01); *A61K 6/77* (2020.01); *A61K 6/78* (2020.01)

(58) Field of Classification Search
None
See application file for complete search history.

(56) References Cited

U.S. PATENT DOCUMENTS 4,269,824 A * 5/1981 Villamarin ............... A61K 8/65 424/70.13
4,351,847 A * 9/1982 Griffith ................... A61P 31/12 514/662
4,438,096 A * 3/1984 Preston ................ C11D 3/0089 424/70.13
7,741,381 B2 * 6/2010 Nakata ..................... A61K 6/30 523/116
8,735,464 B2 * 5/2014 Skaria .................... A61K 6/893 525/126
2001/0033849 A1 * 10/2001 Di Pierro ............. A61K 8/9789 424/769
2012/0021383 A1 * 1/2012 Skaria .................... A61K 6/893 528/80
2013/0011453 A1 * 1/2013 Latta ....................... A61P 29/00 424/401
2013/0041067 A1 * 2/2013 Skaria .................... A61K 6/893 525/126
2017/0239155 A1 * 8/2017 Hartnett ................. A61K 8/375
2020/0017709 A1 * 1/2020 Wang ................... C09D 151/08

* cited by examiner

*Primary Examiner* — Peter A Salamon

(57) ABSTRACT

A gingival barrier protective resin includes 40 to 70 parts of a matrix resin, 20 to 40 parts of a diluent resin, 5 to 20 parts of an inorganic filler, 5 to 20 parts of an ointment base, 0.1 to 0.5 parts of an initiator, 1 to 5 parts of a co-initiator, and 0.1 to 1 part of a polymerization inhibitor.

14 Claims, 2 Drawing Sheets

GINGIVAL BARRIER PROTECTIVE RESIN

RELATED APPLICATIONS

The present patent document claims the benefit of priority to Chinese Patent Application No. 202512002517.5, filed Dec. 29, 2025, the entire content of which is incorporated herein by reference.

BACKGROUND

1. Technical Field

The present disclosure relates to the field of dental materials and in particular to a gingival barrier protective resin.

2. Background Information

In the field of dental treatment, particularly during in-office tooth bleaching procedures, high-concentration bleaching agents or bonding procedures involving strong acids, can cause chemical burns if they come into contact with delicate gingival tissues, leading to whitening of the soft tissue, ulcers, pain, and even atrophy, thereby posing significant discomfort and risks to patients. The core function of a gingival barrier protective resin is to accurately physically isolate the gingiva from these harmful irritants, creating a safe, dry, and controllable operating area.

BRIEF SUMMARY

The present disclosure provides a gingival barrier protective resin, comprising, by weight, 40-70 parts of a matrix resin, 20-40 parts of a diluent resin, 5-20 parts of an inorganic filler, 5-20 parts of an ointment base, 0.1-0.5 parts of an initiator, 1-5 parts of a co-initiator, and 0.1-1 part of a polymerization inhibitor.

BRIEF DESCRIPTION OF THE DRAWINGS

The drawings in the specification, which constitute a part of the present disclosure, are used to provide further understanding of the present disclosure. The illustrative embodiments of the present disclosure and their descriptions are for explanation purposes and do not constitute improper limitations on the present disclosure.

DETAILED DESCRIPTION OF THE DRAWINGS AND THE PRESENTLY PREFERRED EMBODIMENTS

Figure 1:
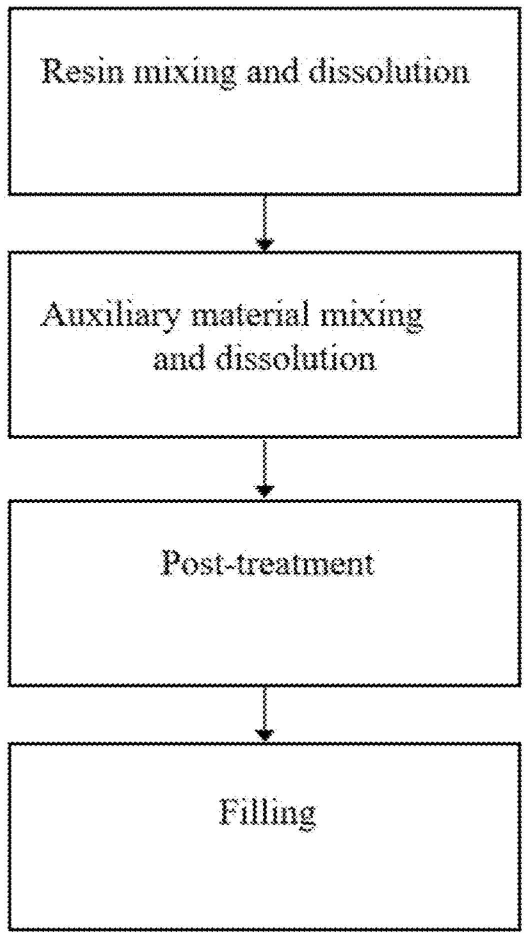
FIG. 1 is a flow chart illustrating the preparation of the gingival barrier protective resin.

Embodiments of the emulsion system and its preparation method in the present disclosure are described below with reference to the accompanying drawings. However, unnecessary detailed descriptions may be omitted. For example, details of matters that are already well known and repetitive descriptions of substantially identical structures may be omitted. This is intended to avoid unnecessarily lengthy descriptions and to facilitate understanding by those skilled in the art. In addition, the accompanying drawings and the following description are provided to enable those skilled in the art to fully understand the present disclosure and are not intended to limit the subject matter recited in the claims.

The 'ranges' disclosed in the present disclosure are defined in terms of lower and upper limits. A given range is defined by selecting a lower limit and an upper limit, which sets the boundaries of the particular range. The ranges defined in this manner may include or exclude the endpoints and may be combined in any arbitrary manner, that any lower limit can be combined with any upper limit to form a range. For example, where ranges of 60 to 120 and 80 to 110 are specified for a given parameter, it is contemplated that the ranges of 60 to 110 and 80 to 120 are also encompassed. Furthermore, where minimum range values of 1 and 2 and maximum range values of 3, 4, and 5 are specified, all of the following ranges are contemplated: 1 to 3, 1 to 4, 1 to 5, 2 to 3, 2 to 4, and 2 to 5. In the present disclosure, unless otherwise specified, a numerical range expressed as "a to b" represents a shorthand expression for any combination of real numbers between a and b, inclusive, wherein both a and b are real numbers. For example, the numerical range "0 to 5" is intended to explicitly disclose all real numbers between 0 and 5, and "0 to 5" is merely a shorthand representation of all such numerical values. In addition, the definition of a parameter as an integer $\geq 2$, explicitly discloses that the parameter may be, for example, integers 2, 3, 4, 5, 6, 7, 8, 9, 10, 11, 12, etc.

Unless otherwise specified, all embodiments and optional embodiments of the present disclosure may be combined with each other to form new technical solutions, and such technical solutions are considered to be disclosed within the content of the present disclosure.

Unless specifically otherwise, all technical features and optional technical features of the present disclosure may be combined with each other to form new technical solutions, and such technical solutions are considered to be disclosed within the content of the present disclosure.

Unless otherwise specified, all steps of the present disclosure may be carried out in order or in a random sequence. For example, if the method includes steps (a) and (b), this indicates that the method may include steps (a) followed by (b), or steps (b) followed by (a). For example, if the method further includes step (c), this indicates that step (c) can be added in any sequence to the method; for instance, the method may include steps (a), (b), and (c), or steps (a), (c), and (b), or steps (c), (a), and (b), etc.

In the present disclosure, the terms "plurality of" or "multiple" refer to two or more.

Unless otherwise specified, the terminology used in the present disclosure has the commonly understood meanings as understood by those skilled in the art.

Unless otherwise specified, the numerical values of the parameters mentioned in the present disclosure can be measured by various testing methods commonly used in the art, for example, by the testing methods described in the embodiments of the present disclosure.

Currently, conventional resins may focus on material strength and durability, and their compositions may contain more fillers to enhance structural strength, making them unsuitable for gingival restorative materials. In contrast, the gingival barrier resin is designed with a special formulation that emphasizes the addition of biocompatible materials to ensure harmonious interaction with gingival tissues.

In the field of gingival restorative materials, the gingival barrier protective resin is a light-curable material used for filling crown defects and restoring teeth after root canal treatment, applied in the gingival sulcus and along the gingival margin. Before curing, the gingival barrier resin can flow beneath the gingiva, better reaching the gingival margin and providing improved aesthetic results; after curing, the gingival barrier protective resin forms a mechanical barrier that effectively isolates bacteria from entering periodontal tissues and reduces irritation to the gingival margin, thereby providing effective protection from external harm and promoting faster gingival healing.

In the related art, many gingival barrier protective resins exhibit high exotherm, which can easily cause burns to the gingival soft tissue. Their thixotropy is often inadequate, leading to poor marginal sealing and, consequently, leakage of chemical irritants, causing adverse reactions such as gingival burning and itching. Therefore, it is necessary to develop a novel gingival barrier protective resin with low exotherm and high thixotropy, capable of reliably isolating corrosive bleaching agents such as peroxides and effectively reducing adverse reactions caused by curing heat and chemical leakage.

To address the issues of high exotherm and poor thixotropy of gingival barrier protective resins in the related art, the present disclosure provides a gingival barrier protective resin including the following compositions in parts by weight: 40-70 parts of matrix resin, 20-40 parts of diluent resin, 5-20 parts of inorganic filler, 5-20 parts of ointment base, 0.1-0.5 parts of initiator, 1-5 parts of co-initiator, and 0.1-1 part of polymerization inhibitor.

In some embodiments, the matrix resin may be 40, 45, 50, 55, 60, 65, 70 parts, or any range formed from these values. In some embodiments, the diluent resin may be 20, 25, 30, 35, 40 parts, or any range formed from these values. In some embodiments, the inorganic filler may be 5, 8, 10, 12, 15, 18, 20 parts, or any range formed from these values. In some embodiments, the initiator may be 0.1, 0.2, 0.3, 0.4, 0.5 parts, or any range formed from these values. In some embodiments, the co-initiator may be 1, 2, 3, 4, 5 parts, or any range formed from these values. In some embodiments, the polymerization inhibitor may be 0.1, 0.2, 0.3, 0.4, 0.5, 0.6, 0.7, 0.8, 0.9, 1 part, or any range formed from these values.

In some embodiments, the matrix resin is selected from one or more of the group consisting of polyurethane acrylate, polyurethane dimethacrylate, and 1,6-hexanediol dimethacrylate. For example, in some embodiments, the matrix resin includes polyurethane dimethacrylate and polyurethane acrylate in a mass ratio of (15-20):(10-15). In some embodiments, the matrix resin includes polyurethane dimethacrylate, polyurethane acrylate, and 1,6-hexanediol dimethacrylate in a mass ratio of (15-20):(10-15):(5-10). In some embodiments, the matrix resin includes polyurethane dimethacrylate, polyurethane acrylate, and 1,6-hexanediol dimethacrylate in a mass ratio of (15-18):(10-12):(5-8).

Polyurethane dimethacrylate, improve marginal sealing performance features due to that it features a mild exothermic reaction, a low peak temperature, and a low volumetric shrinkage during polymerization, and polyurethane dimethacrylate exhibits advantages of high rigidity and high strength after curing. Polyurethane acrylate shows features of rapid curing, exhibits high flexibility and high elasticity after curing, and is easy to be removed in an integral sheet. 1,6-Hexanediol dimethacrylate is characterized by low shrinkage, low water absorption, and low toxicity, thereby improving the durability and biocompatibility of the product. The matrix resins differ in their respective properties. When polyurethane dimethacrylate, polyurethane acrylate, and 1,6-hexanediol dimethacrylate are compounded within the mass ratio ranges specified in the present disclosure, an excellent synergistic effect can be achieved, such as low exotherm, a moderate curing rate, and sufficient curing, thereby improving marginal sealing performance and facilitating removal as a whole piece.

In some embodiments, the diluent resin includes triethylene glycol dimethacrylate. Triethylene glycol dimethacrylate is used to regulate the flowability of the resin system, and its methacrylate groups form a cured network with the matrix resin through radical polymerization reactions, enhancing the mechanical properties of the material, balancing curing speed and volume shrinkage, and reducing internal stress. In other embodiments, the diluent resin may also include resins that have a function similar to that of the methacrylate groups.

In some embodiments, the inorganic filler is selected from one or more of the group consisting of fumed silica, abrasive silica, zirconia. In some embodiments, the inorganic filler includes fumed silica, abrasive silica, and zirconia in a mass ratio of (15-20):(1-5):(3-8). Among these inorganic fillers, the fumed silica provides a thickening and abrasive effect and enhances the hardness and wear resistance of the material through a three dimensional network structure; the abrasive silica enhances the bonding strength with the resin matrix and improves wear resistance; and the zirconia significantly enhances the mechanical strength and heat resistance of the resin matrix.

In some embodiments, the ointment base includes at least one of cetyl alcohol and stearyl alcohol. In some embodiments, the ointment base includes cetyl alcohol and stearyl alcohol in a mass ratio of (50-60):(25-30). Thixotropy refers to the property where viscosity decreases under shear force and increases again when the shear force is stopped. The ointment base and inorganic filler exhibit thixotropy. By incorporating the ointment base and inorganic filler into the gingival barrier protective resin, the thixotropy and marginal sealing effect of the gingival barrier protective resin can be improved, the flexibility after curing can be enhanced, and it can be easily removed as a whole piece.

In some embodiments, the initiator includes at least one of camphorquinone and Phenylbis(2,4,6-trimethylbenzoyl) phosphine oxide. In some embodiments, the initiator includes camphorquinone and Phenylbis(2,4,6-trimethylbenzoyl)phosphine oxide in a mass ratio of (50-60):(40-5).

In some embodiments, the co-initiator includes ethyl 4-dimethylaminobenzoate and its derivatives. The present disclosure employs the synergistic effect of the initiator and co-initiator to enhance initiation efficiency and ensure that the reaction proceeds efficiently at low temperatures.

In some embodiments, the polymerization inhibitor includes at least one of 4-tert-butylcatechol and 4-hydroxyanisole. In some embodiments, the polymerization inhibitor includes 4-tert-butylcatechol and 4-hydroxyanisole in a mass ratio of 2:1.5. The polymerization inhibitor functions by terminating free radical chain reactions, preventing the resin from undergoing self-polymerization during storage or processing, thereby extending the material's shelf life. During the reaction process, it also prevents premature reactions and, in combination with the initiator and co-initiator, jointly optimizes the resin's performance.

In some embodiments, the gingival barrier protective resin includes a pigment in an amount of 0.01-0.1 parts by weight. In some embodiments, the pigment is 0.01, 0.02, 0.03, 0.04, 0.05, 0.06, 0.07, 0.08, 0.09, or 0.1 parts by weight, or any range formed by any of the aforementioned values.

In some embodiments, the pigment is selected from one or more of the group consisting of blue pigment, yellow pigment, white pigment, orange pigment, and purple pigment. In some embodiments, the pigment includes a blue pigment. The blue pigment may include phthalocyanine blue (PB15), indanthrone (PB60), the yellow pigment may include lightfast yellow G (PY1), permanent yellow GR (PY13), the white pigment may include titanium dioxide, the orange pigment may include permanent orange G, and the purple pigment may include quinacridone violet. Other pigments can also be selected as needed.

Since the concentrations of the initiator and co-initiator affect the curing heat and curing rate, in some embodiments, the mass ratio of the matrix resin, the diluent resin, the initiator, and the co-initiator is (40-70):(20-40):(0.1-0.5):(1-5). When the ratios of the initiator, co-initiator, matrix resin, and diluent resin are within the above range, the resulting gingival barrier protective resin can reduce the curing heat while maintaining curing efficiency. When the proportions of the matrix resin, diluent resin, initiator, and co-initiator are outside the range of (40-70):(20-40):(0.1-0.5):(1-5), for example, if the content of at least one of the matrix resin and diluent resin is too high, the curing time is prolonged, leading to excessive curing heat that may burn the gingival soft tissue; if too low, the curing time is shortened, and the cured resin may lack flexibility. Similarly, if the content of at least one of the initiator and co-initiator is too high, the curing rate is too fast, generating excessive heat; if too low, the generation of free radicals decreases, significantly reducing the polymerization rate and potentially preventing complete curing of the resin.

Through the synergistic effect of the matrix resin, the diluent resin, the initiator, the co-initiator, and the polymerization inhibitor, the present disclosure provides a system with low heat generation and a moderate curing rate, thereby reducing the risk of burning the gingival soft tissue due to curing heat. Combined with the properties of the inorganic filler and ointment base, the system exhibits high thixotropy, closely adheres to the gingiva, reliably isolates corrosive bleaching agents such as peroxides, effectively reduces adverse reactions such as gingival burning and itching caused by curing heat and chemical leakage, is easy to apply, and has good flexibility after curing and can be peeled off in one piece.

The compositions in the above embodiments are not limited to the specific compositions listed and may include other compositions having the same or similar effects, which will not be repeated here.

As shown in FIG. 1, the preparation process of the gingival barrier protective resin includes the following steps.

S1 includes the following steps: adding a matrix resin and a diluent resin into a reaction vessel, stirring at a first stirring speed of 20-40 rpm, adding an ointment base maintaining the material system temperature at 60° C.-70° C., and then perform mixing at the first stirring speed to obtain a first mixture. S1 includes mixing and dissolving the resin, which can ben performed by using a jacketed heating reaction vessel with jacket heating turned on. The temperature of the material system may be 60° C., 62° C., 65° C., 68° C., or 70° C., etc. The matrix resin, the diluent resin, and the ointment base are present in amounts of 40-70 parts by weight, 20-40 parts by weight, and 5-20 parts by weight, respectively.

S2 includes the following steps: the system temperature is cooled to 35° C.-40° C. and, under light-protected conditions, an initiator, a co-initiator, and a polymerization inhibitor are gradually added and stirred at the first stirring speed until fully dissolved and uniformly dispersed, followed by addition of an inorganic filler and continued stirring at a second stirring speed to obtain a second mixture. The system temperature may be adjusted to 39.5° C., 39° C., 38.5° C., 38° C., 37.5° C., 37° C., 36.5° C., 36° C., 35.5° C., or 35° C., etc. The initiator, the co-initiator, the polymerization inhibitor, and the inorganic filler are present in amounts of 0.1-0.5 parts by weight, 1-5 parts by weight, 0.1-1 part by weight, and 5-20 parts by weight, respectively.

In some embodiments, the first stirring speed ranges from 20 rpm to 40 rpm, such as 20 rpm, 23 rpm, 25 rpm, 28 rpm, 30 rpm, 33 rpm, 35 rpm, 38 rpm or 40 rpm, etc. In some embodiments, the second stirring speed ranges from 800 rpm to 1000 rpm, such as 800 rpm, 850 rpm, 900 rpm, 950 rpm or 1000 rpm, etc.

S3 includes the following steps: subjecting the second mixture to vacuuming to obtain the gingival barrier protective resin. S3 serves as a post-treatment process in which continuous vacuuming is performed until the paste becomes smooth, dense, and free of bubbles so as to obtain the gingival barrier protective resin.

In some embodiments, the vacuuming degree is controlled at not less than −0.096 Mpa, and the vacuuming time is 30-60 min, such as 30 min, 35 min, 40 min, 45 min, 50 min, 55 min or 60 min, etc.

In some embodiments, the method further includes S4: the resin is further filled into medical-grade disposable syringes using an automatic filling machine under a light-protected yellow lighting environment.

Figure 2:
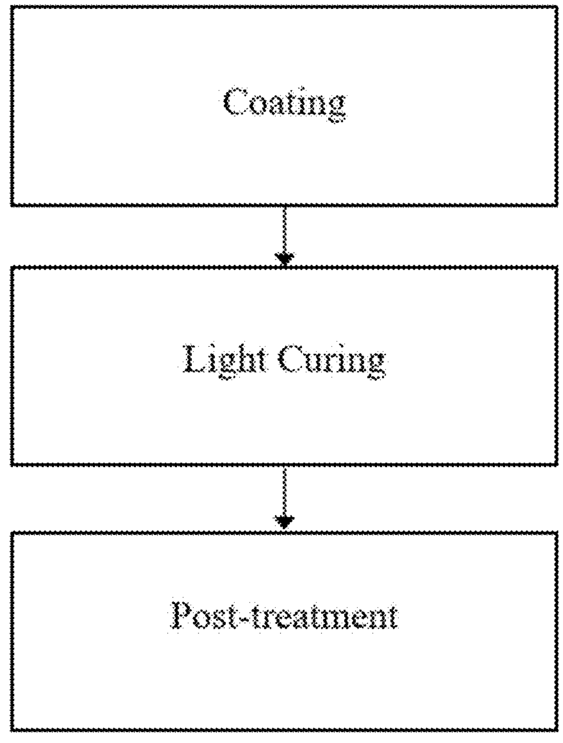
FIG. 2 is a flow chart illustrating the use of the gingival barrier protective resin.

As shown in FIG. 2, the usage process of the gingival barrier protective resin includes the following steps.

S1: the resin is applied to the gingival sulcus and gingival margin to fully seal the sulcus and margin and cover the attached gingiva by 1.5 mm-2 mm (e.g., 1.5 mm, 1.6 mm, 1.7 mm, 1.8 mm, 1.9 mm, 2 mm) with a thickness of 1 mm-3 mm (e.g., 1 mm, 1.2 mm, 1.5 mm, 1.8 mm, 2 mm, 2.5 mm, 2.8 mm, 3 mm), "covering the attached gingiva 1.5 mm-2 mm" refers to the width from the gingival margin toward the crown direction ensuring complete sealing of the sulcus and partial coverage of the attached gingiva to form an effective isolation barrier.

S2: a dental light-curing device is used to irradiate the applied resin with the distance between the light-curing head and the resin being 5 mm to 10 mm (e.g., 5 mm, 6 mm, 7 mm, 8 mm, 9 mm, 10 mm, etc.), the irradiation time being 30 s, and the UV light power of the dental curing lamp being 1800-2500 mw/cm$^2$ (e.g., 1800 mw/cm$^2$, 1900 mw/cm$^2$, 2000 mw/cm$^2$, 2200 mw/cm$^2$, 2500 mw/cm$^2$, etc.).

S3: after dental treatment is completed, the cured barrier resin can be gently pulled from both ends to remove it.

The following description provides a further elaboration of the present disclosure in connection with specific embodiments. It should be noted that, provided there is no conflict, any of the embodiments described below or any of the technical features can be freely combined to form new embodiments. In the following embodiments, all materials are commercially available and will not be described in detail herein. Unless otherwise specified, all contents in the above embodiments are expressed as weight percentages (wt %).

I. Examples 1-5

The formula is shown in Table 1.

TABLE 1

| Raw Material Name | | Example 1 | Example 2 | Example 3 | Example 4 | Example 5 |
|---|---|---|---|---|---|---|
| Matrix Resin | Polyurethane Dimethacrylate | 27 | 27 | 25 | 20 | 37 |
| | Polyurethane Acrylate | 13 | 13 | 18 | 17 | 19 |
| | 1,6-Hexanediol Diacrylate | 1 | 6.2 | / | / | 9 |
| Diluent Resin | Triethylene Glycol Dimethacrylate | 40 | 35 | 37 | 40 | 20 |
| Inorganic Filler | Abrasive Silica | / | / | 3 | 5 | / |
| | Fumed Silica | 8.5 | 8.1 | 5 | 5 | 6.1 |
| | Zirconia | | 1 | 2.1 | 2.5 | 1 |
| Ointment Base | Cetyl alcohol | 8.5 | / | 4.8 | 4 | 4 |
| | Stearyl alcohol | / | 8 | 2.4 | 4 | 2 |
| Initiator | Camphorquinone | 0.5 | 0.5 | 0.4 | 0.2 | 0.2 |
| | Phenylbis(2,4,6-Trimethylbenzoyl) Phosphine oxide | / | / | 0.1 | 0.2 | / |
| Co-initiator | Ethyl 4-dimethylaminobenzoate | 1.7 | 1.5 | 1.5 | 1.3 | 1.0 |
| Polymerization inhibitor | 4-Tert-butylcatechol | 0.5 | 0.5 | 0.5 | 0.5 | 0.5 |
| | 4-Hydroxyanisole | 0.2 | 0.2 | 0.2 | 0.2 | 0.2 |
| Pigment | Blue pigment | 0.1 | 0 | 0 | 0.1 | 0 |

II. Comparative Examples 1-5

TABLE 2

| Raw Material Name | | Example 1 | Example 2 | Example 3 | Example 4 | Example 5 |
|---|---|---|---|---|---|---|
| Matrix | Polyurethane Dimethacrylate | / | 20 | 15 | 37 | 37 |
| Resin | Polyurethane Acrylate | / | / | 5 | 19 | 19 |
| | 1,6-Hexanediol Diacrylate | / | / | / | 9 | 9 |
| Diluent Resin | Triethylene Glycol Dimethacrylate | 80 | 60 | 60 | 20 | 20 |
| Ointment Base | Cetyl alcohol | 8.5 | 8.5 | 8.5 | 9.15 | 8.5 |
| | Stearyl alcohol | 8.5 | 8 | 8.5 | 4 | 4 |
| Initiator | Camphorquinone | 0.5 | 0.5 | 0.4 | 0.05 | 0.6 |
| | Phenylbis(2,4,6-Trimethylbenzoyl) Phosphine oxide | / | / | 0.1 | / | 0.1 |
| Co-initiator | Ethyl 4-dimethylaminobenzoate | 1.7 | 1.7 | 1.7 | 1.0 | 1.0 |
| Polymerization inhibitor | 4-Tert-butylcatechol | 0.5 | 0.5 | 0.5 | 0.5 | 0.5 |
| | 4-Hydroxyanisole | 0.2 | 0.2 | 0.2 | 0.2 | 0.2 |
| Pigment | Blue pigment | 0.1 | 0.1 | 0.1 | 0.1 | 0.1 |

The formula is shown in Table 2.

The preparation method of the above embodiments is as follows.

1. Add the matrix resin and diluent resin into a jacketed reactor, start low-speed stirring (30 rpm) and initiate jacket heating. Add the ointment base, maintain the temperature of the material at 60-70° C., and continue stir until complete dissolution is achieved and the solution becomes clear and transparent.
2. Switch to jacket cooling water circulation and cool the material to 35-40° C. Under light-avoiding conditions and low-speed stirring (30 rpm), gradually add the initiator, the co-initiator, the polymerization inhibitor, and the pigment until they are fully dissolved and uniformly dispersed; maintain the material temperature at 35-40° C. throughout the process.
3. Slowly adding the inorganic filler. After all the material has been added, increase the stirring speed to high speed (900 rpm) until the paste becomes uniform and fine, and maintain the material temperature at 35-40° C. throughout the process.
4. Apply vacuum under controlled the pressure of at not less than −0.096 MPa, and continue for 45 minutes until the paste becomes smooth, fine, dense and free of bubbles.
5. Under light-avoiding yellow lighting, use an automatic filling machine to dispense the paste into medical-grade disposable syringes.

The preparation method of the formulation in the comparative examples is as follows.

1. Add the matrix resin and diluent resin into a jacketed reactor, start low-speed stirring (30 rpm) and initiate jacket heating. Add the ointment base, maintain the material temperature at 60-70° C., and continue stirring until complete dissolution is achieved and the solution becomes clear and transparent.

2. Switch to jacket cooling water circulation and cool the material to 35-40° C. Under light-avoiding conditions and low-speed stirring (30 rpm), gradually add the initiator, the co-initiator, the polymerization inhibitor, and the pigment until they are fully dissolved and uniformly dispersed, and maintain the material temperature at 35-40° C. throughout the process.
3. Vacuumize by controlling the vacuum pressure at not less than −0.096 MPa, and continue for 45 minutes until the paste becomes smooth, fine, dense and free of bubbles.
4. Under light-avoiding yellow lighting, use an automatic filling machine to dispense the paste into medical-grade disposable syringes.

III. Performance Testing and Results

1. Test Samples: Examples 1-5, Comparative Examples 1-5

2. Test Method (1) Curing Test: apply the sample (same sample) to the gingival sulcus and gingival margin, thoroughly seal the gingival sulcus and margin, and cover it to 1.5 mm of the attached gingiva with a thickness of 1 mm. Irradiate the coated dental gingival barrier protection resin, with a dental light-curing unit, with the lamp head at a distance of 5 mm from the resin. After use, the cured barrier resin can be removed by gently pulling from both ends. Curing conditions: irradiate with an LED light-curing lamp with an intensity of 2000 mW/cm$^2$ and a wavelength of 470 nm; record the curing time of the sample and the exothermic temperature (tested with a thermocouple).

(2) Curing Depth Test: fill the sample into a 6 mm long groove, irradiate one end with an LED curing lamp with an intensity of 2000 mW/cm$^2$ and a wavelength of 470 nm. After curing, scrape off the uncurled viscous sample with a scraper, and measure the length of the cured sample.

(3) Vertical Flow Test: apply the sample to the vertical surface of a simulated dental arch and test for any sliding or flowing within one hour.

(4) Thixotropy Test: a rotational viscometer is used, operating at a shear rate of 0.1 s$^{-1}$, and the stable viscosity value at this low shear rate is recorded. The shear rate is then gradually increased to 100 s$^{-1}$, and the stable viscosity value at this high shear rate is recorded. The ratio of these two values is calculated.

(5) Extrusion Test: using a texture analyzer with a probe simulating an injection needle, the sample is squeezed at a constant speed, and the extrusion force is recorded.

(6) Flexural Strength Test: place a specimen with dimensions of 40 mm in length, 4 mm in width, and 3 mm in thickness horizontally on supporting cylinders. Apply a vertical force with the loading head aligned to the center, and record the maximum load at fracture (accurate to 0.1 N) and deflection.

The formation of flexural strength:

$$\sigma = \frac{3PL}{2bh^2}$$

Where P denotes the fracture load (N), L denotes the span (mm), b denotes the width (mm), and h denotes the thickness (mm).

3. The test results are shown in Table 3 below.

TABLE 3

| Sample | Curing time/s | Exothermic temperature/° C. | Curing Depth/ mm | Vertical Flowability | Viscosity ratio | Extrusion Force/N | Flexural strength/ Mpa |
|---|---|---|---|---|---|---|---|
| Example 1 | 30 | 2.1 | 2.7 | No sagging or flowing | 4.8 | 24 | 105 |
| Example 2 | 32 | 2.2 | 2.5 | No sagging or flowing | 4.6 | 25 | 100 |
| Example 3 | 28 | 2.0 | 2.6 | No sagging or flowing | 4.6 | 25 | 102 |
| Example 4 | 35 | 2.3 | 2.6 | No sagging or flowing | 4.2 | 25 | 90 |
| Example 5 | 25 | 2.2 | 2.7 | No sagging or flowing | 4.7 | 25 | 105 |
| Comparative Sample 1 | 80 | 4.5 | 1.8 | sagging and flowing | 1.5 | 36 | 65 |
| Comparative Sample 2 | 70 | 4.0 | 1.9 | sagging and flowing | 1.4 | 37 | 75 |
| Comparative Sample 3 | 70 | 4.2 | 1.9 | sagging and flowing | 1.6 | 38 | 75 |

TABLE 3-continued

| Sample | Curing time/s | Exothermic temperature/° C. | Curing Depth/ mm | Vertical Flowability | Viscosity ratio | Extrusion Force/N | Flexural strength/ Mpa |
|---|---|---|---|---|---|---|---|
| Comparative Sample 4 | 60 | 4.4 | 2.0 | sagging and flowing | 1.3 | 40 | 100 |
| Comparative Sample 5 | 20 | 5.5 | 2.7 | sagging and flowing | 1.3 | 40 | 104 |

As shown in Table 3, the gingival barrier protective resin provided by the present disclosure can be completely cured within 30 seconds under irradiation by a 2000 mW/cm$^2$ LED curing lamp. The exothermic temperature during curing ranges from 2° C. to 2.3° C., and the curing depth is between 2.5 mm and 2.7 mm. The vertical flow test is passed, with no sagging observed within one hour. The ratio of low-shear viscosity to high-shear viscosity is between 4.2 and 4.8, the extrusion force ranges from 24 N to 26 N, and the flexural strength is between 90 MPa and 105 MPa. In contrast, comparative examples 1-5 fail the vertical flow test, exhibiting sagging within one hour. Their low-shear to high-shear viscosity ratio ranges from 1.3 to 1.6, and the extrusion force is between 36 N and 40 N, indicating that the abrasive properties of comparative examples 1-5 are inferior to those of embodiments 1-5. Furthermore, comparative examples 1-3 show a curing time of 70-80 seconds, an exothermic temperature of 4.2-4.5° C., a curing depth of 1.8-1.9 mm, and a flexural strength of 65-75 MPa. This demonstrates that comparative examples 1-3 cure more slowly, generate higher heat, achieve shallower curing depth, and have lower flexural strength compared to embodiments 1-4. Comparative Example 4, as compared to Embodiment 5, exhibits a slower curing time, a higher exothermic temperature, and a reduced curing depth. In contrast, Comparative Example 5, as compared to Embodiment 5, exhibits a faster curing time while still showing a higher exothermic temperature.

The gingival barrier protective resin obtained in the present disclosure exhibits a low exothermic temperature and a moderate curing rate, thereby preventing thermal damage to the gingival soft tissue during curing. The resin demonstrates high thixotropy, enabling it to closely adhere to the gingiva and reliably isolate corrosive bleaching agents, such as peroxides, effectively avoiding adverse effects such as gingival burning, itching, or discomfort caused by exothermic curing and leakage of chemical irritants. Furthermore, the resin is readily applicable, and once cured, it possesses good flexibility and can be removed intact as a single piece.

The above embodiments are merely some embodiments of the present disclosure and shall not be construed as limiting the scope of protection of the present disclosure. Any modifications or substitutions that do not substantially alter the technical solution, and that would be made by those skilled in the art based on the present disclosure, are intended to fall within the scope of protection as claimed herein.

The invention claimed is:

1. A gingival barrier protective resin comprising the following compositions in parts by weight: 40-70 parts of a matrix resin, 20-40 parts of a diluent resin, 5-20 parts of an inorganic filler, 5-20 parts of an ointment base, 0.1-0.5 parts of an initiator, 1-5 parts of a co-initiator, and 0.1-1 part of a polymerization inhibitor wherein the matrix resin comprises polyurethane dimethacrylate, polyurethane acrylate, and 1,6-hexanediol dimethacrylate in a mass ratio of (15-20):(10-15):(5-10).

2. The gingival barrier protective resin according to claim 1, wherein the diluent resin comprises triethylene glycol dimethacrylate.

3. The gingival barrier protective resin according to claim 1, wherein the inorganic filler comprises one or more selected from the group consisting of fumed silica, abrasive silica, and zirconia.

4. A gingival barrier protective resin, comprising the following compositions in parts by weight: 40-70 parts of a matrix resin, 20-40 parts of a diluent resin, 5-20 parts of an inorganic filler, 5-20 parts of an ointment base, 0.1-0.5 parts of an initiator, 1-5 parts of a co-initiator, and 0.1-1 part of a polymerization inhibitor;

wherein the inorganic filler comprises fumed silica, abrasive silica, and zirconia in a mass ratio of (15-20):(1-5):(3-8).

5. The gingival barrier protective resin according to claim 1, wherein the ointment base comprises at least one of cetyl alcohol and stearyl alcohol.

6. A gingival barrier protective resin, comprising the following compositions in parts by weight: 40-70 parts of a matrix resin, 20-40 parts of a diluent resin, 5-20 parts of an inorganic filler, 5-20 parts of an ointment base, 0.1-0.5 parts of an initiator, 1-5 parts of a co-initiator, and 0.1-1 part of a polymerization inhibitor;

wherein the ointment base comprises cetyl alcohol and stearyl alcohol in a mass ratio of (50-60):(25-30).

7. The gingival barrier protective resin according to claim 1, wherein the initiator comprises at least one of camphorquinone and phenylbis(2,4,6-trimethylbenzoyl)phosphine oxide.

8. A gingival barrier protective resin, comprising the following compositions in parts by weight: 40-70 parts of a matrix resin, 20-40 parts of a diluent resin, 5-20 parts of an inorganic filler, 5-20 parts of an ointment base, 0.1-0.5 parts of an initiator, 1-5 parts of a co-initiator, and 0.1-1 part of a polymerization inhibitor;

wherein the initiator comprises camphorquinone and phenylbis(2,4,6-trimethylbenzoyl)phosphine oxide in a mass ratio of (50-60):(40-50).

9. The gingival barrier protective resin according to claim 1, wherein the co-initiator comprises ethyl 4-dimethylaminobenzoate and derivatives of ethyl 4-dimethylaminobenzoate.

10. The gingival barrier protective resin according to claim 1, wherein the polymerization inhibitor comprises at least one of 4-tert-butylcatechol and 4-hydroxyanisole.

11. The gingival barrier protective resin according to claim 10, wherein the polymerization inhibitor comprises 4-tert-butylcatechol and 4-hydroxyanisole in a mass ratio of 2:1.5.

12. The gingival barrier protective resin according to claim 1, further comprises 0.01-0.1 parts by weight of a pigment, wherein the pigment is selected from one or more of the group consisting of blue pigment, yellow pigment, white pigment, orange pigment, and purple pigment.

13. The gingival barrier protective resin according to claim 1, wherein the resin is prepared by the following steps:

S1: adding the matrix resin and the diluent resin into a reaction vessel and stirring at a first stirring speed, then adding the ointment base while maintaining a system temperature of 60-70° C., and continuing to stir at the first stirring speed to obtain a first mixture;

S2: lowering the system temperature to 35-40° C., under light-protected conditions, gradually adding the initiator, the co-initiator, and the polymerization inhibitor into the first mixture; stirring at the first stirring speed until all the compositions are completely dissolved and uniformly dispersed, then continuing to add the inorganic filler, and after completion of the addition inorganic filler, stirring at a second stirring speed to obtain a second mixture; and S3: subjecting the second mixture to vacuum to obtain the gingival barrier protective resin.

14. The gingival barrier protective resin according to claim 13, wherein the first stirring speed is ranged from 20 to 40 rpm, the second stirring speed is ranged from 800 to 1000 rpm, the vacuum degree during vacuuming is controlled to be not less than −0.096 MPa, and the vacuuming time is ranged from 30 to 60 minutes.

* * * * *